United States Patent [19]
Bell et al.

[11] 3,969,427
[45] July 13, 1976

[54] CONVERSION OF ALCOHOLS AND/OR ETHERS TO HYDROCARBONS

[75] Inventors: Weldon K. Bell, Pennington; Clarence D. Chang, Princeton, both of N.J.

[73] Assignee: Mobil Oil Corporation, New York, N.Y.

[22] Filed: Dec. 20, 1974

[21] Appl. No.: 535,053

[52] U.S. Cl. .................... 260/676 R; 260/677 XA; 260/682; 260/683.9
[51] Int. Cl.² ...................... C07C 9/02; C07C 9/14
[58] Field of Search ............. 260/676 R, 683.9, 668, 260/682, 677 XA

[56] References Cited
UNITED STATES PATENTS

| | | | |
|---|---|---|---|
| 1,979,841 | 11/1934 | Pier et al. ........................ | 260/676 R |
| 2,049,058 | 7/1936 | Gleason et al. ................. | 260/668 R |
| 2,492,984 | 1/1950 | Grosse et al. ................... | 260/676 R |
| 3,203,998 | 8/1965 | House et al. .................... | 260/676 R |

Primary Examiner—Herbert Levine
Attorney, Agent, or Firm—Charles A. Huggett; Michael G. Gilman

[57] ABSTRACT

Conversion of lower alcohols or their corresponding ethers or halides alone or in admixture to conjunct mixtures of hydrocarbon products by catalyzing the conversion with a molten salt bath of zinc chloride with or without potassium chloride with cofed hydrogen.

3 Claims, No Drawings

CONVERSION OF ALCOHOLS AND/OR ETHERS TO HYDROCARBONS

This invention relates to the conversion of alcohols and/or ethers. It more particularly refers to the conversion of the organic oxygenates using a molten salt catalyst reaction environment.

U.S. Pat. No. 2,492,984 to Grosse reported the conversion of dimethyl ether in molten zinc chloride. The products were hydrocarbons of various chain lengths and isomeric configurations. Most importantly large quantities of coke were coproduced in this conversion making it less than totally satisfactory for consideration as a commercially useful conversion.

U.S. Pat. No. Re. 28,128 to Hardesty et al. shows the conversion of heavy petroleum stocks in a molten zinc chloride salt bath. This patent is particularly concerned with hydrocracking heavy petroleum stocks such as shale oil, tar sands oil, coal oil, residua, heavy vacuum gas oil and the like with hydrogen in molten zinc chloride along with potassium chloride, or the like to produce a product of substantially lower average molecular weight and boiling range than the feed. The conditions of operation are relatively typical hydrocracking conditions.

The disclosed process of the Grosse patent is sometimes modified to include an alkali metal halide, typically potassium chloride, in order to reduce viscosity and promote hydrocarbon separation. This addition has been found to reduce activity for the conversion of dimethyl ether to hydrocarbons. In fact, one might say that the potassium chloride actually supressed production of hydrocarbons.

It is, therefore, an object of this invention to provide an improved process for converting lower organic hetero atom containing compounds to hydrocarbon products using a fused salt reaction medium.

Other and additional objects of this invention will become apparent from a consideration of this entire specification including the claims hereof.

As used herein, the term "conjunct mixture of hydrocarbon products" means a mixture of hydrocarbons which does not particularly correspond to the size (number of carbon atoms) or isomeric configuration of the hydrocarbon portion of the reactant or any integral multiple thereof. This definition is not intended to exclude some common chain length and/or isomeric configurations from the product, but rather is intended to characterize the hydrocarbon product as a mixture of diverse compounds. It is obvious that if the reactant is a one carbon moiety, such as methanol, any product will have the same isomeric configuration and an even multiple of carbon atoms. This term has been used previously in the chemical literature, albeit in a different specific portion thereof, with the same meaning, see Schmerling, L. and V. N. Ipatieff, Advances in Catalysis II, 1950, 21–80, at p. 22, 62.

Therefore, in accord with and fulfilling these objects, one aspect of this invention resides in carrying out the conversion of lower organic alcohols, ethers and/or halides in a molten salt bath catalyst under such conditions as to minimize coke formation and yet maintain a significant conversion of reactant to hydrocarbons, particularly a conjunct mixture of hydrocarbons. The conversion takes place at about 570° to 750°F, 0 to 1500 psig and 0.1 to 20 WHSV. It is an essential feature of this invention to cofeed hydrogen along with the organic reactant. The proportion of hydrogen to reactant is suitably about 10 to 1 on a molar basis, preferably about 2 to 0.5 to 1.

The hydrogen can be fed as a pure gas or in admixture with other materials, e.g. synthesis gas, a mixture of carbon monoxide and hydrogen.

It is important to note that the reactants suitable for use in this invention have up to about 8 carbon atoms in one or more hydrocarbon portions attached to an oxygen or halogen atom. The preferred reactants are methanol, dimethyl ether and/or methyl chloride. While it may be preferred to utilize a reactant consisting essentially of any oxygen or halogen organic compound or mixture thereof as described, the reactant can also include one or more hydrocarbon compounds or fractions. These may coreact with each other and/or may react intra-murally.

The molten salt bath comprises zinc chloride. It may contain up to about 50 mole percent potassium chloride. The reaction may be carried out in a batch or continuous system. In batch, the molen salt and the reactant are commonly agitated for a time sufficient to carry out the reaction to a desired degree of completion. In a continuous system, the reaction zone may contain a suitable amount of molten salt and the reactant vaporized and bubbled through. The reactant and molen salt may be passed countercurrent or cocurrent to each other.

An essential feature of this invention is the cofeeding of hydrogen to the system. It has been found that the presence of hydrogen in the system reduces coke formation. It is most interesting to note than in addition to a reduction in coke make, the cofeeding of hydrogen seems to significantly change the product distribution causing the product to be more saturated as one might expect, but also causing the product to have a much higher molecular weight hydrocarbon materials. The hydrogen should be provided under a partial pressure of about 15 to 1500 psig and in an amount of about 0 to 3600 SCF per pound mole of feed. Hydrogen recycle can be used.

The following Examples are illustrative of the practice of this invention without being limiting thereon. Parts and percentages are by weight unless expressly stated to be on some other basis.

Examples 1, 2 and 3

Methanol was converted by passing such through molten zinc chloride at 617°F and one (1) atm. pressure. Hydrogen and helium were cofed as specified. The results of these runs are set forth below:

TABLE 1

| Run No. | Gas | Gas feed rate (ml/min) | Methanol feed rate (ml/min) | Coke make (% of carbon in feed converted to coke) |
|---|---|---|---|---|
| 1. | $H_2$ | 19 | 1.3 | 18 |
| 2. | He | 21 | 21.0 | 22 |
| 3. | $H_2$ | 69 | 12.5 | 17 |

Examples 4 and 5

Dimethyl ether was converted by passing such through molten zinc chloride at 617°F and 41 atm. pressure. The ether was fed at a rate of 7.96 ml/hour and hydrogen or helium gas was cofed at a rate of 85 ml/min (STP).

TABLE 2

| Run No. | 4 | 5 |
|---|---|---|
| Gas | He | H$_2$ |
| Product Distribution % | | |
| Carbon Dioxide | 0.7 | 0.8 |
| Methanol | 1.0 | 1.4 |
| Dimethyl Ether | 15.6 | 19.4 |
| Methyl Chloride | 9.0 | 37.3 |
| Coke | 21.1 | 2.1 |
| Hydrocarbons | 52.3 | 39.1 |
| Hydrocarbon Distribution % | | |
| C$_1$ | 0.7 | 0.2 |
| C$_2$ | 3.9 | 0.3 |
| C$_3$ | 9.3 | 6.0 |
| C$_4$ | 47.2 | 38.3 |
| C$_5$ | 11.7 | 15.6 |
| C$_6$ | 14.5 | 13.3 |
| C$_7$ | 3.5 | 5.6 |
| C$_{8+}$ | 9.3 | 21.7 |
| C$_5^+$ gasoline | 39 | 56 |
| i-C$_4$/n-C$_4$° | 18 | 16 |
| i-C$_5$/n-C$_5$° | 60 | 50 |
| C$_2$°/C$_2$= | 0.39 | 0.75 |
| C$_3$°/C$_3$= | 2.2 | 4.3 |
| C$_4$°/C$_4$= | 25 | 40 |

If zinc oxide is produced in this process by reaction of zinc chloride with water, it can be regenerated to zinc chloride by known procedures.

What is claimed is:

1. In the process of converting a feed of at least one member selected from the group consisting of lower organic alkyl alcohols, ethers, and halides to conjunct hydrocarbon mixtures by bubbling a substantial amount of said feed as a vapor through a molten salt comprising zinc chloride at about 570 to 750°F; the improvement which comprises cofeeding hydrogen in a proportion of about 180 to 3600 SCF per pound mol of feed at a pressure of about 0 to 1500 psig into admixture with said vapor and passing said admixture through said molten salt.

2. The improved process claimed in claim 1 wherein said feed is at least one member selected from the group consisting of methanol, dimethyl ether, methyl chloride and mixtures thereof.

3. The improved process claimed in claim 1 wherein methyl chloride is produced from methanol or dimethyl ether, and said methyl chloride is converted in contact with molten zinc chloride and hydrogen.

* * * * *

UNITED STATES PATENT AND TRADEMARK OFFICE
CERTIFICATE OF CORRECTION

PATENT NO. : 3,969,427
DATED : July 13, 1976
INVENTOR(S) : WELDON K. BELL and CLARENCE D. CHANG It is certified that error appears in the above-identified patent and that said Letters Patent are hereby corrected as shown below:

Column 2, line 37, "higher molecular weight hydrocarbon materials. The" should be --higher proportion of higher molecular weight hydrocarbon materials. The--.

Signed and Sealed this

Eighteenth Day of January 1977

[SEAL]

Attest:

RUTH C. MASON
*Attesting Officer*

C. MARSHALL DANN
*Commissioner of Patents and Trademarks*